June 24, 1941. R. L. RAGIN Plant Pat. 477

SEEDLESS PINEAPPLE ORANGE

Filed Oct. 14, 1939

R. L. Ragin Inventor

By Mason Fenwick & Lawrence Attorneys

Patented June 24, 1941

Plant Pat. 477

UNITED STATES PATENT OFFICE

477

SEEDLESS PINEAPPLE ORANGE

Robert Lee Ragin, Shiloh, Fla., assignor to George W. Clapp, doing business as Clapp & Clapp, Orlando, Fla.

Application October 14, 1939, Serial No. 299,552

1 Claim. (Cl. 47—62)

This invention is an improvement in oranges known as pineapple oranges in Florida, largely grown for commercial purposes and relates to a new variety of pineapple orange characterized by seedlessness.

I first observed this new variety in June 1934, in an orange grove in the Lyratta area of Turnbull Hammock, Brevard County, Florida. It occurred as a single limb sport on an ordinary pineapple orange tree. This limb was under my observation during a period of two growing seasons during which time it came true to the original observation of seedlessness and in the meantime I had taken budwood from this limb with the permission of the owner and propagated trees by the method of shield budding in my nursery, for experimental purposes and further observation. I have reproduced trees by the method of shield budding on young sour orange seedlings through two (2) generations. These have now borne fruit. By these means it has been definitely established that this is not only a new and desirable variety of pineapple orange, but that it reproduces readily and true to type.

The accompanying drawing illustrates a fruit of my new variety of pineapple orange, the foliage and wood of the tree being omitted as they do not form novel features of the new variety and correspond to those of the known pineapple orange.

Figure 1:
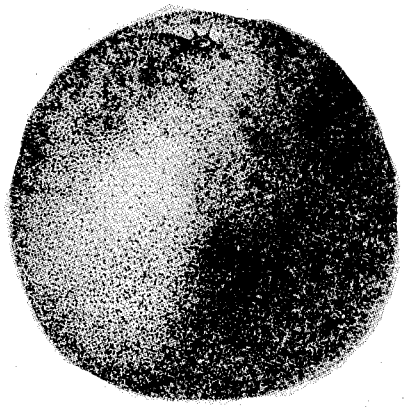
Figure 1 is a view in perspective, the stem end being shown.
Figure 2:
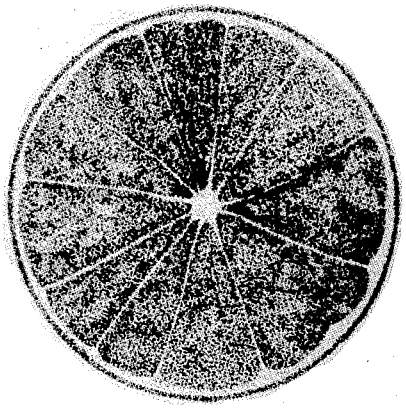
Figure 2 is a transverse section in a plane perpendicular to the axis of the fruit.

A more detailed description follows:

The tree has the same appearance and characteristics as the well known pineapple orange tree and has the same heavy and early bearing characteristics. The size, shape and color of the leaves are apparently the same as found in the well known pineapple orange tree.

*Blossoming and fruiting habits.*—This new variety of seedless pineapple orange blossoms at practically the same time as the regular pineapple orange tree. It has the same facility for producing large crops of fruit as the regular seeded variety of pineapple orange tree. The botanical structure of the fruit is the same as that of the fruit of the pineapple orange tree grown commercially in Florida except that my new variety is seedless, or not having more than one to five (1 to 5) seeds in rare fruits showing seeds, (the common commercial pineapple orange has from thirteen (13) to twenty-three (23) seeds per fruit). The central core is very small, the sections nearly touching through the middle of the fruit.

*Ripening of fruit.*—This new seedless variety of pineapple orange matures its fruit at practically the same season of the year as the regular commercial variety of pineapple orange. The major portions of the crop mature during December, January and February in Florida.

*Quality of fruit.*—The color, amount of rag and the tenderness of the flesh, and the amount and flavor of the juice and the odor are practically the same as in the regular pineapple orange.

*Description of fruit.*—Form somewhat variable, varying from nearly round to slightly oblate, occasional specimens being quite compressed; size medium to large, 2½ by 2¾ inches; $2\frac{15}{16}$ by 3¼ inches; color deep orange, full ripe well-colored specimens show a reddish tinge; apex rounded or very slightly depressed and scarred; base rounded, very smooth; calyx small, blunt; rind smooth, bright, glossy and satiny, ⅛ inch thick; oil cells small, quite conspicuous, flush with surface or slightly elevated; sections eleven (11), irregular, flesh or medium grain, orange-yellow; juice sacs pointed, spindle-shaped, small; juice abundant, yellowish in color; pulp melting; acidity and sweetness well blended; flavor excellent, rich vinous, sprightly; pith solid, or very nearly solid, small, $\frac{3}{16}$ inch to ½ inch; seeds lacking (occasional fruit will show one (1) to five (5) seeds); most fruit shows no seeds. Season: December, January and February although it may sometimes be held later.

What I claim is:

A new and distinct variety of orange and orange tree of the pineapple type as described, characterized by the seedlessness of its fruit, as shown.

ROBERT LEE RAGIN.